United States Patent
Janevski et al.

(10) Patent No.: US 8,762,072 B2
(45) Date of Patent: Jun. 24, 2014

(54) METHOD OF DETERMINING A RELIABILITY INDICATOR FOR SIGNATURES OBTAINED FROM CLINICAL DATA AND USE OF THE RELIABILITY INDICATOR FOR FAVORING ONE SIGNATURE OVER THE OTHER

(75) Inventors: Angel Janevski, New York, NY (US); Nilanjana Banerjee, Armonk, NY (US); Yasser Alsafadi, Yorktown Heights, NY (US); Vinay Varadan, Hastings on Hudson, NY (US)

(73) Assignee: Koninklijke Philips N.V., Eindhoven (NL)

( * ) Notice: Subject to any disclaimer, the term of this patent is extended or adjusted under 35 U.S.C. 154(b) by 266 days.

(21) Appl. No.: 13/119,742

(22) PCT Filed: Sep. 24, 2009

(86) PCT No.: PCT/IB2009/054176
§ 371 (c)(1),
(2), (4) Date: Mar. 18, 2011

(87) PCT Pub. No.: WO2010/038173
PCT Pub. Date: Apr. 8, 2010

(65) Prior Publication Data
US 2011/0173201 A1  Jul. 14, 2011

Related U.S. Application Data

(60) Provisional application No. 61/102,032, filed on Oct. 2, 2008.

(51) Int. Cl.
*G01N 33/48* (2006.01)
*G06G 7/58* (2006.01)

(52) U.S. Cl.
USPC ............................................. 702/19; 703/11

(58) Field of Classification Search
None
See application file for complete search history.

(56) References Cited

PUBLICATIONS

Blum, A., et al.; Combining Labeled and Unlabeled Data with Co-Training; 1998; Proc. Conf. on Computational Learning Theory; pp. 92-100.
Harris, C., et al.; Biomarker discovery across annotated and unannotated microarray datasets using semi-supervised learning; 2008; BMC Genomics, Biomed Central; vol. 9(2)57-62.
Li, T., et al.; Semisupervised learning from different information sources; 2005; Knowledge and Information Systems; an International Journal; 7(3)289-309.
Li, T., et al.; Gene functional classification by semi-supervised learning from heterogeneous data; 2003; Proc. of 2003 ACM Symposium on Applied Computing; pp. 78-82; http://portal.acm.org/citation/cfm?id=952552.
Schaffer, J. D., et al.; A Genetic Algorithm Approach for Discovering Diagnostic Patterns in Molecular Measurement Data; 2005; Proc. IEEE Symposium on Computational Intelligence in Bioinformatics and Computational Biology; 8 pages.

*Primary Examiner* — Eric S Dejong

(57) ABSTRACT

This invention relates to a method and an apparatus for determining a reliability indicator for at least one set of signatures obtained from clinical data collected from a group of samples. The signatures are obtained by detecting characteristics in the clinical data from the group of sample sand each of the signatures generate a first set of stratification values that stratify the group of samples. At least one additional and parallel stratification source to the signatures obtained from group of sample sis provided, the at least one additional and parallel stratification source to the signatures being independent from the signatures and generates a second set of stratification values. A comparison is done for each respective sample, where the first stratification values are compared with a true reference stratification values, and where the second stratification values are compared with the true reference stratification values. The signatures are assigned with similarity measure indicators indicating whether the first and the second stratification values match with the true reference stratification values. These are then implementing as input in determining the reliability of the signatures.

20 Claims, 2 Drawing Sheets

METHOD OF DETERMINING A RELIABILITY INDICATOR FOR SIGNATURES OBTAINED FROM CLINICAL DATA AND USE OF THE RELIABILITY INDICATOR FOR FAVORING ONE SIGNATURE OVER THE OTHER

CROSS REFERENCE TO RELATED APPLICATIONS

This application claims the benefit of U.S. provisional application ser. no. 61/253,884 filed Oct. 22, 2009, which is incorporated herein by reference.

FIELD OF THE INVENTION

The present invention relates to a method and an apparatus for determining a reliability indicator for at least one set of signatures obtained from clinical data collected from a group of samples, the signatures being obtained by detecting characteristics in the clinical data from the group of samples, where each of the signatures generate a first set of stratification values that stratify the group of samples.

BACKGROUND OF THE INVENTION

High-throughput molecular measurements are often subjected to analyses for the purpose of clinical applications to identify patterns in datasets that help stratify biological samples. One such application is a selection of feature subsets, e.g. from gene expression data, that can be used as diagnostic signatures for a particular category of patients. Such diagnostic signatures may be used for clinical diagnosis of disease, disease staging and/or therapy choice (e.g. positive and negative response of a therapy regiment for some disease). It should be noted that the clinical states of the patients are typically known during the discovery of such signatures. This "ground truth" is often available as part of the clinical study from which the samples are obtained, or it may be known from detecting some molecular property using a molecular measurement other than the one used for the signatures discovery (e.g. DNA methylation, proteomics, and SNP). It is common for a wide variety of statistical and machine learning algorithms to be applied to such datasets in order to discover patterns among these measurements that are diagnostic, i.e. can be used to discriminate the clinical states. In addition, the awareness is growing among biologists and clinicians that it is unlikely that single-variable (univariate) signatures will be discovered for most diseases and conditions of interest; multi-variable (multivariate) signatures are believed to be necessary which increases the combinatorial challenge of the signature discovery. One difficulty that plagues this domain is that the datasets are invariably characterized as being measurement-rich but case-poor, i.e. there are significantly many more measurements than patients. As a consequence, pattern discovery methods become prone to discovering spurious patterns, i.e. patterns that predict well on the given data, but poorly on new cases. This is also called overfitting. Various schemes for reducing the number of measurements by discarding some believed to be of low quality or unlikely to be related to the clinical question, such as schemes for re-sampling and cross-validation, have been applied to overcome overfitting, but the problem cannot be completely overcome by theses methods.

BRIEF DESCRIPTION OF THE INVENTION

The object of the present invention is to provide an improved method that overcomes such overfitting problems.

According to one aspect the present invention relates to a method of determining the reliability of at least one set of signatures determined from clinical data collected from a group of samples, the signatures being obtained by detecting characteristics in the clinical data from the group of samples, where each of the signatures generate a first set of stratification values that stratify the group of samples, the method comprising:

providing at least one additional and parallel stratification source to the signatures obtained from said group of samples, the at least one parallel stratification source being independent from the signatures and generates a second set of stratification values for the group of samples, comparing for each respective sample:

the first set of stratification values with true reference stratification values, the second set of stratification values with true reference stratification values, assigning the signatures with similarity measure indicators indicating whether the first and the second stratification values match with the true reference stratification values, and implementing the similarity measure indicators as input in determining the reliability of the signatures.

Thus, it is now possible to compare signatures for their "alignment" with particular parallel stratification criteria and thus help to eliminate spurious patterns.

In one embodiment, the step of implementing the similarity measure indicators as input comprises:

identifying which of the signatures have similarity measure indicators indicating that their stratification values do not match with the true reference stratification values, and for those identified signatures determining an alignment indicator indicating how aligned the stratification values of these signatures are with the stratification values of at least one parallel stratification source, the alignment indicator being indicative to the reliability of the signatures.

For clarification purposes, referring to table I and II in the detailed description, this means that for a signature it is determined for which samples this signature has classified incorrectly compared to the true reference stratification value (in this case, false negative (FN) or false positive (FP)). The second step is to compare these misclassifications with the parallel stratification source, i.e. a further "reliability step" is performed. This comparison shows that two of them match with the parallel stratification source. It should be noted that tables 1 and 2 are primarily intended to list all possible combinations of (mis)classifications and don't paint a realistic example with say 100 or 200 samples.

In one embodiment, the step of determining the alignment indicator comprises determining how often the stratification values of the signatures match with the stratification values generated by at least one parallel stratification source, this number being indicative to the reliability of the signatures.

Referring to table III, said embodiment has an advantage in selecting between three signatures, signature 1, 2 and 3. It should again be noted that this is only for clarification purposes and does not reflect a real scenario where the number of samples would typically be much larger. In this scenario, all the signatures show only 50% correct classification (compared to the true value). In the absence of this additional one or more parallel stratification source, it would not be possible to distinguish between these three signatures. However, by taking a closer look at the table for signature 1, two of the misclassifications match with the parallel stratification source (sample 2 and 4), for signature 2 also two of the misclassifications match with the parallel stratification source (sample 4 and 5) but for signature 3 three of the misclassifications match with the parallel stratification source (sample 2, 5 and 7). In this particular case, the alignment indicator is simply the "counts" (or percentage), i.e. number of matches with the parallel criterion, namely, "2", "2" and "3". Thus, signature 3 would be considered as a more reliable signature than the remaining signatures because 3 out of four misclassifications match with the parallel stratification source.

For further clarification, suppose there are two signatures S1 and S2 obtained e.g. from gene expression that are trying to stratify cancer patients as aggressive and non-aggressive. By only using the signature (basic modality, the gene expression) it is only possible to say that both signatures make e.g. 4 misclassifications and it is thus not possible to move forward with any certainty about which signature is more likely to be clinically or biologically relevant. A parallel stratification source (e.g. a clinical prognostic index) also gives a separate stratification of the same patients into aggressive and non-aggressive. The parallel stratification makes it possible to observe that S2 makes more misclassifications compared to the clinical prognostic index compared to S1. Based on this, one can conclude that S1 is a 'better' signature than S2 because is more 'in line' with the parallel stratification Thus, S1 will have a higher reliability index compared to S2.

In one embodiment, the parallel stratification is based on one or more of the following measurements:
 a clinical information, or
 imaging data, or
 data obtained from high-throughput molecular measurement, or
 biological annotation of the molecular measurements.

In one embodiment, the method further comprises continuously repeating said comparing step, said assignment step and said implementing step until a pre-defined criterion has been met.

In one embodiment, the repeating said comparing steps until a pre-defined criterion has been met is based on implementing the reliability indicator to rank signatures in one step and as a selection criterion for choosing which signatures should be considered in the subsequent step.

Thus, by using such iterative application of the reliability indicator, the effect of overfitting is diminished or at least reduced depending on the stratification power of the parallel criterion.

In one embodiment, the pre-defined criterion includes one or more criteria to end the iterations based on one or more of the following:
 a fixed number of repetitions
 a desired alignment performance
 a desired reliability performance It should be noted that this is not an exhaustive list.

According to another aspect, the present invention relates to a computer program product for instructing a processing unit to execute the above mentioned method steps when the product is run on a computer.

According to still another aspect, the present invention relates to a apparatus for determining a reliability indicator for at least one set of signatures obtained from clinical data collected from a group of samples, the signatures being obtained by detecting characteristics in the clinical data from the group of samples, where each of the signatures generate a first set of stratification values that stratify the group of samples, comprising:
 means for providing at least one additional and parallel stratification source to the signatures obtained from said group of samples, the at least one parallel stratification source being independent from the signatures and generates a second set of stratification values for the group of samples,
 a processor for comparing for each respective sample:
 the first set of stratification values with a true reference stratification values,
 the second set of stratification values with the true reference stratification values,
 a processor for assigning the signatures with similarity measure indicators indicating whether the first and the second stratification values match with the true reference stratification values, and
 a processor for implementing the similarity measure indicators as input in determining the reliability of the signatures.

The aspects of the present invention may each be combined with any of the other aspects. These and other aspects of the invention will be apparent from and elucidated with reference to the embodiments described hereinafter.

BRIEF DESCRIPTION OF THE DRAWINGS

Embodiments of the invention will be described, by way of example only, with reference to the drawings, in which.

DESCRIPTION OF EMBODIMENTS

Figure 1:
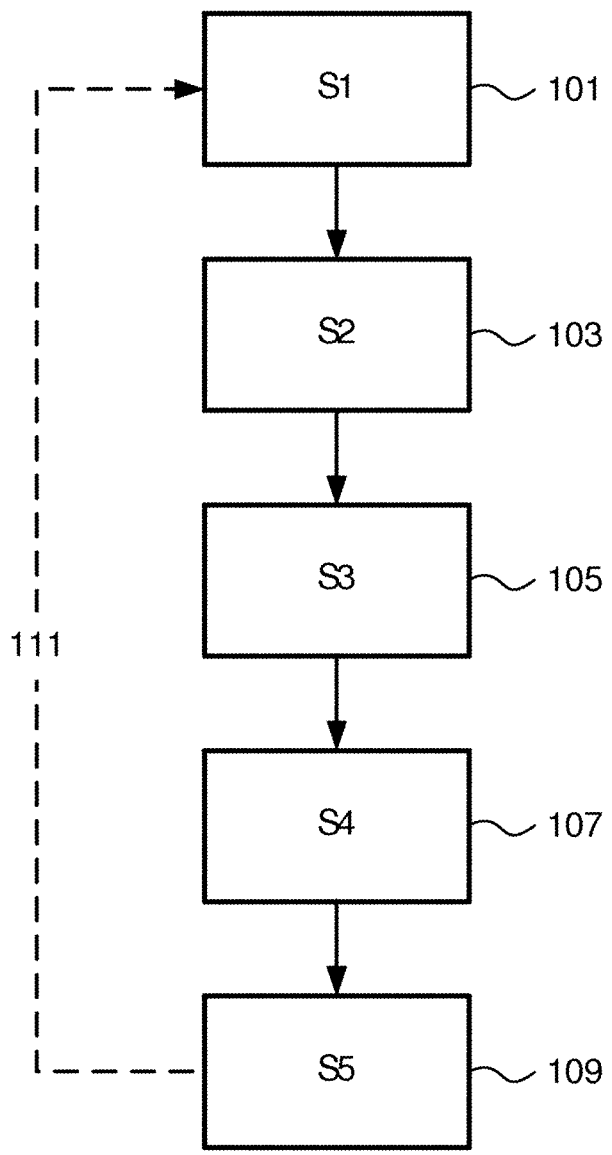
FIG. 1 shows a flowchart of a method according to the present invention.

FIG. 1 shows a flowchart of a method according to the present invention of determining a reliability indicator for at least one set of signatures obtained from clinical data collected from a group of samples.

In step (S1) 101, the signatures are generated by detecting characteristics in the clinical data from the group of samples. The group of samples can as an example comprise samples collected from potential cancer patients and the clinical data can be high-throughput molecular measurements performed on these samples. The result of the analyzing such data will give a set of signatures, i.e. signatures that are characteristics for this particular type of cancer. By the term signatures or also referred to as molecular signatures is meant any characteristics in the clinical data that represent a common feature throughout all the samples. Various methods may be applied of obtaining such signatures, e.g. by using search methods such as a Genetic Algorithm (GA) algorithm, which produces feature subsets that are used to induce a signature that provides test classifications for a set of samples. Further details about such a GA-based experiment may be found in "Schaffer, A. Janevski, and M. Simpson, *"A Genetic Algorithm Approach for Discovering Diagnostic Patterns in Molecular Measurement Data,"* presented at Proceedings of the 2005 IEEE Symposium on Computational Intelligence in Bioinformatics and Computational Biology, CIBCB 2005, La Jolla, CA, USA, 2005"These signatures the first stratification values stratifying the group of samples with respect to the signatures. This means that per sample there is only one stratification assignment, where each sample can be assigned as "aggressive" or "non-aggressive", or labeled as "0" or "1", or even on a specific scale, e.g. from 1-3. Accordingly, in case there are 100 samples each particular signature provides a stratification value, such as a 0 or 1, for each of the 100 samples. signature particular signature provides a stratification value, such as a 0 or 1, for each of the 100 samples.

As discussed previously, the present invention deals with the scenario where the data is not sufficient by itself to guarantee "good" signatures due to the very few samples compared to the relatively large number of measurements. Analysis of such data is prone to finding spurious patterns that accidentally appear to be characterizing the data very well. As will be discussed in more details later, by characterizing the patterns additionally, it is possible to recognize spurious patterns from "real" (more promising) patterns.

In step (S2) 103, at least one parallel stratification sources is provided from said group of samples, where the at least one parallel stratification source is independent from the signatures and generates a second set of stratification values for the group of samples. This means that an additional source for characterization is provided, but where the additional source is obtained using a different method. Accordingly, for each respective sample a parallel stratification source is provided in addition to the signatures, and this parallel stratification source generates a second stratification value, e.g. "aggressive" or "non-aggressive", or "0" or "1". This means that sample 1 is assigned with a stratification value that is e.g. stratifies sample 1 as "non-aggressive", and as an additional source, the parallel stratification source stratifies the sample also as "non-aggressive". Accordingly, one source is the signature obtained from clinical data, and the parallel stratification source may e.g. be obtained from clinical information, e.g. prognostic indices such as the following for breast cancer: Nottingham Prognosis Index (Pinder, Elston et al. 2003), National Institutes of Health Consensus (*NIH* 2001), and the St. Gallen Consensus Conference (Ciatto, Cecchini et al. 1990)). The reason of adding such parallel stratification is to enable comparing the signatures for their "alignment" with particular parallel stratification criteria. This will be discussed in more details later. In general, the aim of the present invention is to go after the same kind of stratification (e.g. aggressive vs. non-aggressive) by using completely different method.

Other examples of such parallel stratification sources are sources obtained from Imaging data, which is data from any relevant imaging modality (MRI, CT, with or without contrast agents) which can be analyzed in such a fashion that stratifies the samples in a similar fashion as the analysis of the "core" e.g. high-throughput molecular measurements. This is typically done by analyzing features of the images (shape, texture, etc) and outputting a category (e.g. aggressive or non-aggressive) for each image/sample. Other parallel stratification sources are high-throughput molecular measurement: gene expression data, DNA methylation, mass-spectrometry proteomics. As long as the data from such measurements is analyzed in a manner that characterizes the samples similarly to the "core" high-throughput measurements, it is possible to use that output to drive the basic signatures discovery process. Yet other parallel stratification sources are annotation: the features in high-throughput molecular measurements can be characterized for example based on their biological properties. A widely used source for annotation for example is Gene Ontology (see geneontology.org), where genes are annotated for their molecular function, biological process, and cellular component. Such annotation can also be used to characterize a set of features (e.g. genes) with respect to say molecular function. This view of the data can then be used in the same way as the other types above to stratify samples.

In step (S3) 105, for each respective sample, comparison steps are performed where the first stratification and the second stratification values are compared with true reference stratification values. The true reference stratification values is considered as the "ground truth" because the data comes from retrospective studies, e.g. in cancer patients, there would be a 5 year, or 10 year follow-up and hence will be known if the cancer returned or not. Accordingly, in this step for sample n, the first stratification value for sample n and the second stratification value for the parallel stratification source (e.g. based on image data) are compared with the ground truth value.

In step (S4) 107, the signatures are assigned with similarity measure indicators indicating whether the first and the second stratification values match with the true reference stratification values. As an example, if the reference stratification value (the ground truth value) for sample n is "aggressive", and the first stratification and the second stratification values are "aggressive" and "non-aggressive", respectively, the similarity measure indicator might be "true" and "false", or "true-positive" and "false-positive". This could also be labeled as "+" and "−". This is repeated for all n samples, i.e. for each respective sample the first stratification and the second stratification values are compared to the true reference stratification values.

TABLE I

| Sample | True reference stratification value | First stratification value | Second stratification value |
|---|---|---|---|
| Sample 1 | aggressive | aggressive | aggressive |
| Sample 2 | aggressive | non-aggressive | aggressive |
| Sample 3 | aggressive | aggressive | non-aggressive |
| Sample 4 | aggressive | non-aggressive | non-aggressive |
| Sample 5 | non-aggressive | aggressive | aggressive |
| Sample 6 | non-aggressive | non-aggressive | aggressive |
| Sample 7 | non-aggressive | aggressive | non-aggressive |
| Sample 8 | non-aggressive | non-aggressive | non-aggressive |

Table I shows an example to illustrate how this method can be implemented in its simplest form using two stratifications, "aggressive" and "non-aggressive" and 8 samples. The first column shows the samples, the second column is the true reference stratification value "ground truth value", the third column is the second stratification value "parallel stratification value" and the fourth column is the first stratification value "the predicted class". Given the "true" class for each test sample, one knows whether the induced signatures correctly predict the class of a sample or not.

Referring to (S4) 107, the assignment of the signatures with similarity measure indicators is shown in Table II. "TP" means "true-positive", "TN" means true-negative, "FP" means false-positive and "FN" means false-negative. Accordingly, for sample 1 as an example, the similarity measure indicator for the parallel stratification is "TP" because the true value says that sample one is an aggressive

TABLE II

| Sample | True reference | Parallel | Signature 1 |
|---|---|---|---|
| Sample 1 | aggressive | TP | TP |
| Sample 2 | aggressive | FN | TP |
| Sample 3 | aggressive | TP | FN |
| Sample 4 | aggressive | FN | FN |
| Sample 5 | non-aggressive | FP | FP |
| Sample 6 | non-aggressive | TN | FP |
| Sample 7 | non-aggressive | FP | TN |
| Sample 8 | non-aggressive | TN | TN | and the first and the second stratification values predicts the same. On the other hand, for sample 2, the parallel stratification predicts negative, whereas the ground truth value predicts positive. Thus, the similarity measure indicator for the second stratification value is "FN" (it predicted negative and it was false), whereas the second stratification value (the predicted class) predicts the same as the ground truth value and is thus given a "TP" (predicted positive and it was true) similarity measure indicator becomes. This is repeated for all the samples.

It should be noted that tables 1 and 2 are primarily intended for clarification and don't paint a realistic example with say 100 or 200 samples.

In one embodiment, it is determined whether the classifications are in agreement with a clinical prognostic index where those misclassifications where the signatures being tested is wrong (FN: false negative or FP: false positive), and the parallel stratification (in this example, the clinical index) is correct (TP: true positive or TN: True negative) is penalized. For simplicity, in this embodiment it is assumed that the clinical prognostic index is fixed (a one-time calculation based on the clinical data). An interesting part is the variable part, i.e. the signatures. One typically wants to reduce the total number of FN and FP. In this embodiment, those signatures which are not correct (e.g. sample 4 and 5) but where the parallel stratification is correct (e.g. samples 3 and 6) are assigned a greater penalty weight than the prediction combinations where both the index and the classifier are not correct (e.g. samples 4 and 5). This is because that one can conclude that the signatures for samples 4 and 5 are more in line with the parallel stratification. Accordingly, in this way it is possible to distinguish between the four signatures (see sample 3-6) by using the parallel stratification as an additional information source. In the absence of this parallel stratification it would be impossible to distinguish between these four "FN" signatures.

In step (S5) 109, the similarity measure indicators are used as input in determining the reliability of the signatures. In one embodiment, the step of using the similarity measure indicators as input is based determining an alignment indicator indicating how aligned the at least one set of signatures are based on the second stratification values of at least one parallel stratification. The alignment indicator may comprises counting the number of matches where the similarity measure indicators of the at least one set signatures matches with the similarity measure indicators of the at least one parallel stratification. The number of matches is then indicative to the reliability of the signatures.

TABLE III

| Sample | True reference | Parallel | Signature 1 | Signature 2 | Signature 3 |
|---|---|---|---|---|---|
| Sample 1 | aggressive | TP | TP | TP | TP |
| Sample 2 | aggressive | FN | FN | TP | FN |
| Sample 3 | aggressive | TP | TP | FN | TP |
| Sample 4 | aggressive | FN | FN | FN | TN |
| Sample 5 | non-aggressive | FP | TP | FP | FP |
| Sample 6 | non-aggressive | TN | FP | TN | TN |
| Sample 7 | non-aggressive | FP | TN | TN | FP |
| Sample 8 | non-aggressive | TN | TN | TN | TN |
| COUNTS | | | 2 | 2 | 3 |

Table III shown an example of multi-similarity where the number of signatures is three, S1-S3, and where one parallel stratification is being used. Table III shows a situation where each signature classifies correctly five of the samples. Thus, in the absence of the parallel stratification it is not possible to distinguish between the three signatures. However, as discussed previously an alignment indicator may be determined simply by counting the number of cases where the signatures classify incorrectly and also does the parallel stratification. For signature 1, two of the misclassifications match with the parallel stratification (sample 2 and 4), for signature 2 also two of the misclassifications match with the parallel stratification (sample 4 and 5) but for signature 3 three of the misclassifications match with the parallel stratification (sample 2, 5 and 7). In this particular case, the alignment indicator is simply the "counts", i.e. number of matches with the parallel stratification, namely, "2", "2" and "3". Thus, signature 3 would be considered as a more reliable signature than the remaining signatures.

This may be expressed in more general way vie a mathematical expression. Assume there are N samples: $S=\{s_1, s_2, \ldots s_N\}$ and M stratification categories: $C=\{c_1, c_2, \ldots c_M\}$ (e.g. aggressive=$c_1$ and non-aggressive=$c_2$). For each sample, a reference stratification value is given:

$$REF=\{<s_i, r_i>|i=1\ldots N, r_i \in C\} \quad (1)$$

The analysis also assigns stratification value to each sample:

$$ANALYSIS=\{<s_i, r_i^1>|i=1\ldots N, r_i^1 \in C\} \quad (2)$$

The parallel criteria also assign stratification value to each sample:

$$PARALLEL=\{<s_i, r_i^2>|i=1\ldots N, r_i^2 \in C\} \quad (3)$$

The similarity measure is basically a function that takes pairs of stratifications:

$$SIMILARITY(<s_i, r_i^1>, <s_i, r_i^2>) \quad (4)$$

and returns some result.

EXAMPLE 1

$$SIMILARITY1(<s_i,r_i^1>,<s_i,r_i^2>)=count(r_i^1 \neq r_i^2).$$

EXAMPLE 2

$$SIMILARITY2(<s_i,r_i^1>,<s_i,r_i^2>)=<count(r_i^1 \neq r_i^2)$$
$$\&r_i^2 cA, count(r_i^1 \neq r_i^2)\&r_i^2=c_B>,$$

where $c_A$ can be say aggressive, and $c_B$ non-aggressive.

This may be referred to as SIMILARITY(ANALYSIS, REF), SIMILARITY(ANALYSIS, PARALLEL), and SIMILARITY(ORTHOGONAL, REF). The reliability indicator is then determined by comparing the results from these calls. In the previous examples, the similarity was based on SIMILARITY(ANALYSIS, ORTHOGONAL).

The example for table III discloses the scenario where simultaneously compare 3 (or more) stratifications are being compared, or a MULTI-SIMILARITY($<s_i, r_i^1>, <s_i, r_i^2>, <s_i, r_i^3>, \ldots$), where it is possible to define the similarity by comparing the input stratifications. The reliability here could actually be same as the similarity, i.e. it may be referred as MULTI-SIMILARITY(ANALYSIS, PARALLEL, REF) as an example.

It should be noted that the signatures might be more consistent with the "true value" and totally inconsistent with the parallel stratification. In this case, the alignment indicator is simply an indicator that might e.g. be determined by an expert simply be monitoring the data.

In one embodiment, new set of signatures are determined and said steps of determining an alignment indicator is repeated. This may e.g. be repeated several hundreds of times. Those that are better in stratifying the samples and are aligned with the parallel stratification source are selected for further evaluation in the subsequent steps. Accordingly, by continuously generating signatures a search is performed resulting in a set of signatures after a number of repetitions. The qualitative improvement using the parallel stratification source makes it possible to continuously drive the search towards a better set of signatures that are more aligned with the parallel stratification(s) and with reduced overfitting compared to the same approach without a parallel stratification. The iterative nature of the signature discovery is discussed in "Schaffer, D., A. Janevski, et al. (2005). *A Genetic Algorithm Approach for Discovering Diagnostic Patterns in Molecular Measurement Data*. Proceedings of the 2005 IEEE Symposium on Computational Intelligence in Bioinformatics and Computational Biology, CIBCB 2005, La Jolla, Calif., USA, IEEE", hereby incorporated as whole by reference.

Figure 2:
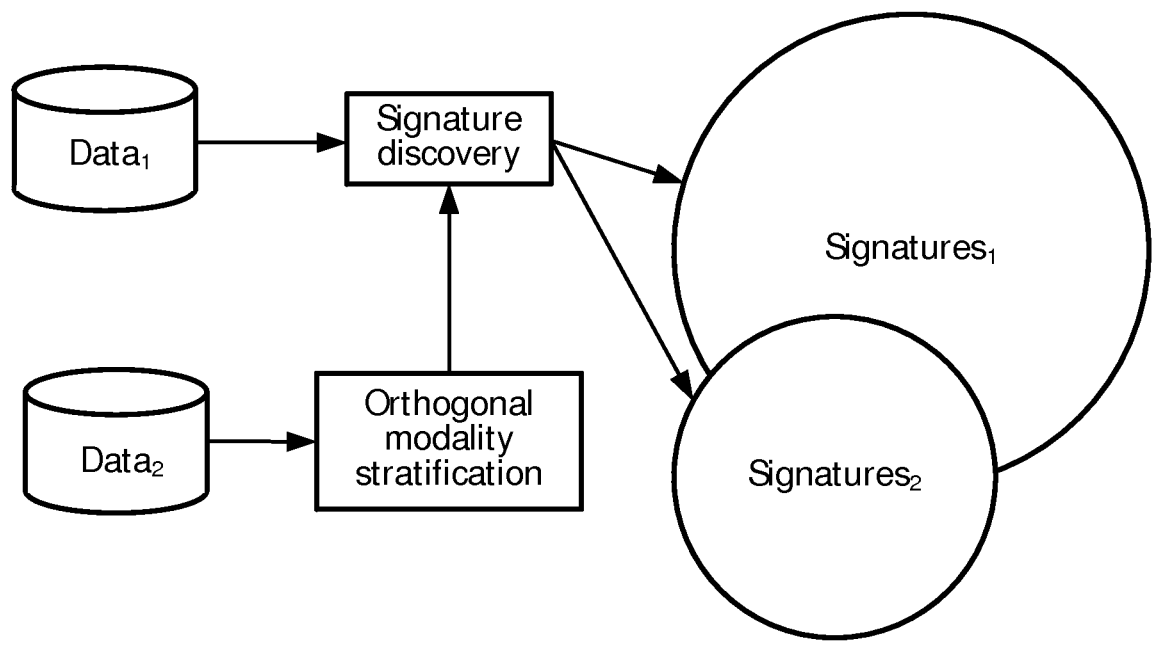
FIG. 2 depicts the addition of an parallel criterion to a signature discovery process.

FIG. 2 depicts graphically the result of such continuous repetition, where Data1 is the "core" modality, i.e. the classifiers which may be obtained through high-throughput molecular measurements dataset. The result of analyzing only this data will give one set of signatures (signatures1). Data 2 is said parallel stratification data. When driving the signature discovery with the parallel stratification; another set of signatures is obtained as output (signatures2). The only requirement is that data1 and data2 are on sample sets that significantly overlap just from different modalities.

Figure 3:
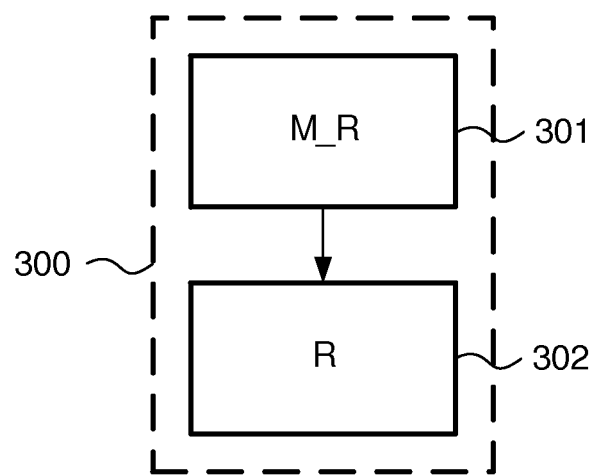
FIG. 3 shows an apparatus according to the present invention.

FIG. 3 shows an apparatus 300 according to the present invention for determining a reliability indicator for at least one set of signatures obtained from clinical data collected from a group of samples. The signatures are obtained by detecting characteristics in the clinical data from the group of samples. Also, the signatures generate the first set of stratification values stratifying the group of samples with respect to the signatures. The apparatus comprises means 301 for providing at least one parallel stratification to the signatures obtained from said group of samples, the at least one parallel stratification being independent from the signatures and generates a second set of stratification values with respect to the parallel stratification. The apparatus also comprises a processor 301 performing the above mentioned method steps in FIG. 1.

Certain specific details of the disclosed embodiment are set forth for purposes of explanation rather than limitation, so as to provide a clear and thorough understanding of the present invention. However, it should be understood by those skilled in this art, that the present invention might be practiced in other embodiments that do not conform exactly to the details set forth herein, without departing significantly from the spirit and scope of this disclosure. Further, in this context, and for the purposes of brevity and clarity, detailed descriptions of well-known apparatuses, circuits and methodologies have been omitted so as to avoid unnecessary detail and possible confusion.

Reference signs are included in the claims, however the inclusion of the reference signs is only for clarity reasons and should not be construed as limiting the scope of the claims.

The invention claimed is:

1. A method of determining a reliability indicator for at least one set of signatures determined from clinical data collected from a group of samples, the signatures being obtained by detecting characteristics in the clinical data from the group of samples, where each of the signatures generate a first set of stratification values that stratify the group of samples, the method comprising:

providing at least one additional stratification source to the signatures obtained from said group of samples, wherein the at least one additional stratification source is independent from the signatures and generates a second set of stratification values for the group of samples, comparing, by a processing system, the first set of stratification values with true reference stratification values to provide a first set of similarity measure indicators for each signature, comparing, by the processing system, the second stratification values with true reference stratification values to provide a second set of similarity measure indicators, and determining, by the processing system, the reliability of the signatures based on at least one of: differences between the first and second set of similarity measure indicators, and matches between the first and second set of similarity measure indicators.

2. A method according to claim 1, wherein determining the reliability of the signatures includes, for each signature:

identifying which of indicators of the set of first similarity measure indicators of the signature indicate that their stratification value does not match with the true reference stratification value, and for those identified indicators:

determining an alignment indicator indicating how aligned the stratification values of these indicators are with the corresponding second stratification values of the at least one additional stratification source, the alignment indicator being indicative of the reliability of the signature.

3. A method according to claim 2, wherein determining the reliability of the signatures includes, for each signature determining a count of how often the first stratification values of the signatures match with the second stratification values generated by at least one additional stratification source, this count being indicative to the reliability of the signature.

4. A method according to claim 1, wherein the at least one additional stratification source is based on one or more of the following measurements:

a clinical information, imaging data, data obtained from high-throughput molecular measurement, or biological annotation of the molecular measurements.

5. A method of according to claim 1, further comprising continuously repeating, until a pre-defined criterion has been met:

generating an other set of stratification values;

comparing the other set of stratification values with true reference stratification values to provide an other set of similarity measure indicators; and determining the reliability of the signatures based on at least one of: differences between the other set and the second set of similarity measure indicators, and matches between the other set and the second set of similarity measure indicators.

6. A method according to claim 5, wherein repeating until a pre-defined criterion has been met includes ranking the signatures, and selecting which signatures should be considered in the subsequent repeating based on the ranking of the signatures.

7. A method according to claim 5, wherein the pre-defined criterion includes one or more criteria to end the iterations based on one or more of the following:

a fixed number of repetitions, a desired alignment performance, and a desired reliability performance.

8. A method according to claim 1, wherein determining the reliability of the signatures includes, for each signature determining a count of how often the first stratification values of the signatures match with the second stratification values generated by at least one additional stratification source, this count being indicative to the reliability of the signature.

9. An apparatus for determining a reliability indicator for at least one set of signatures comprising:
  a memory that receives:
    a first set of stratification values obtained by detecting characteristics in clinical data collected from a group of samples for at least one set of signatures, and
    a second set of stratification values based on at least one additional stratification source that is independent of the signatures;
  a processor that, for each respective sample:
    compares the first set of stratification values in the memory with a true reference stratification values to provide a first set of similarity measure indicators,
    compares the second set of stratification values in the memory with the true reference stratification values to provide a second set of similarity measure indicators; and
    determines the reliability of the signatures based on at least one of: differences between the first and second set of similarity measure indicators, and matches between the first and second set of similarity measure indicators.

10. The apparatus of claim 9, wherein the processor determines the reliability of the signatures by a process that includes, for each signature:
  identifying which of indicators of the set of first similarity measure indicators of the signature indicate that their stratification value does not match with the true reference stratification value, and for those identified indicators:
  determining an alignment indicator indicating how aligned the stratification values of these indicators are with the corresponding second stratification values of the at least one additional stratification source, the alignment indicator being indicative of the reliability of the signature.

11. The apparatus of claim 9, wherein the processor determines the reliability of the signatures by a process that includes, for each signature: determining a count of how often the first stratification values of the signatures match with the second stratification values generated by at least one additional stratification source, this count being indicative to the reliability of the signature.

12. The apparatus of claim 9, wherein the at least one additional stratification source is based on one or more of the following measurements:
  a clinical information,
  imaging data,
  data obtained from high-throughput molecular measurement, or
  biological annotation of the molecular measurements.

13. The apparatus of claim 9, wherein processor repeats, until a pre-defined criterion has been met:
  receiving an other set of stratification values;
  comparing the other set of stratification values with true reference stratification values to provide an other set of similarity measure indicators; and
  determining the reliability of the signatures based on at least one of: differences between the other set and the second set of similarity measure indicators, and matches between the other set and the second set of similarity measure indicators.

14. A non-transitory computer readable medium that includes a program that, when executed by a processor, causes the processor to determine a reliability indicator for at least one set of signatures determined from clinical data collected from a group of samples, the signatures being obtained by detecting characteristics in the clinical data from the group of samples, by:
  receiving, for each of the signatures, a first set of stratification values that stratify the group of samples,
  receiving a second set of stratification values for the group of samples based on at least one additional stratification source that is independent from the signatures,
  comparing the first set of stratification values of each signature with true reference stratification values to provide a first set of similarity measure indicators,
  comparing the second stratification values with true reference stratification values to provide a second set of similarity measure indicators, and
  determining the reliability of the signatures based on at least one of: differences between the first and second set of similarity measure indicators and matches between the first and second set of similarity measure indicators.

15. The medium of claim 14, wherein the program causes the processor to determine the reliability of the signatures by a process that includes, for each signature:
  identifying which of indicators of the set of first similarity measure indicators of the signature indicate that their stratification value does not match with the true reference stratification value, and for those identified indicators:
  determining an alignment indicator indicating how aligned the stratification values of these indicators are with the corresponding second stratification values of the at least one additional stratification source, the alignment indicator being indicative of the reliability of the signature.

16. The medium of claim 14, wherein the program causes the processor to determine the reliability of the signatures by a process that includes, for each signature:
  determining a count of how often the first stratification values of the signatures match with the second stratification values generated by at least one additional stratification source, this count being indicative to the reliability of the signature.

17. The medium of claim 14, wherein the at least one additional stratification source is based on one or more of the following measurements:
  a clinical information,
  imaging data,
  data obtained from high-throughput molecular measurement, or
  biological annotation of the molecular measurements.

18. The medium of claim 14, wherein the program causes the processor to repeat, until a pre-defined criterion has been met:
  receiving an other set of stratification values;
  comparing the other set of stratification values with true reference stratification values to provide an other set of similarity measure indicators; and
  determining the reliability of the signatures based on at least one of: differences between the other set and the second set of similarity measure indicators, and matches between the other set and the second set of similarity measure indicators.

19. The medium of claim 17, wherein program causes the processor to rank the signatures, and select which signatures should be considered in a subsequent repeat based on the ranking of the signatures.

20. The medium of claim 17, wherein the pre-defined criterion includes one or more criteria to end the iterations based on one or more of the following:
  a fixed number of repetitions,
  a desired alignment performance, and
  a desired reliability performance.

* * * * *